United States Patent [19]

Bailey et al.

[11] Patent Number: 5,198,547
[45] Date of Patent: Mar. 30, 1993

[54] PROCESS FOR N5-FORMYLATING TETRAHYDROPTERIDINES

[75] Inventors: Steven W. Bailey; June E. Ayling, both of Mobile, Ala.

[73] Assignee: South Alabama Medical Science Foundation, USA, Mobile, Ala.

[21] Appl. No.: 851,733

[22] Filed: Mar. 16, 1992

[51] Int. Cl.$^5$ .......................................... C07D 475/04
[52] U.S. Cl. ................................. 544/258; 544/257; 544/259; 544/260; 544/261; 544/298; 544/320; 544/322; 544/326; 548/236; 560/170; 564/194; 564/355
[58] Field of Search ............... 544/261, 258, 259, 260, 544/279, 257; 548/336

[56] References Cited

U.S. PATENT DOCUMENTS 2,742,468  4/1956  Brockman et al. ................. 544/260
4,148,999  4/1979  Temple et al. ...................... 544/258
4,670,563  1/1987  Jansen et al. ....................... 548/336
4,937,342  6/1990  Kurono et al. ..................... 544/258

FOREIGN PATENT DOCUMENTS 0138995  2/1985  European Pat. Off. ........... 514/249
0266042  6/1988  European Pat. Off. ........... 544/258

OTHER PUBLICATIONS

Theilheimer, "Synthetic Methods" vol. 18, p. 210, entry 472 (1964).
Bailey et al., 1978, J. Biol. Chem. 253, pp. 1598–1605.
Kwee et al., 1980, 5th Int. Symp. on Bioelectrochemistry, pp. 693–698.
Sugimoto et al., 1980, Bull. Chem. Soc. Japan 53, pp. 3385–3386.
Matsuura et al., 1981, Bull. Chem. Soc. Japan 54, pp. 2543–2544.
Lazarus, et al., 1981, Biochemistry 20, pp. 6834–6841.
Doyle et al., 1983, 7th Int. Symp. on Pteridines and Folic Acid Derivatives, pp. 85–89.
Bailey et al., 1983, Biochemistry 22, pp. 1790–1798.
Matsuura et al., 1985, Heterocycles 23, pp. 3115–3120.
Rees et al., 1986, Tetrahedron 42, pp. 117–136.
Khalifa et al., 1980, Helv. Chim. Acta 63, pp. 2554–2558.
Forsch et al., 1985, J. Org. Chem. 50, pp. 2582–2583.
Sato et al., 1986, Anal. Biochem. 154, pp. 516–524.
Smith et al., 1949, J. Biol. Chem. 180, pp. 1209–1223.
Dess et al., 1983, J. Org. Chem. 48, pp. 4155–4156.

Primary Examiner—Donald G. Daus

[57] ABSTRACT

Intermediates and a process for the synthesis of 6-monosubstituted tetrahydropteridine C6-stereoisomers, including (6S)-tetrahydrofolic acid. The intermediates are shown in their two enantiomeric forms as follows:

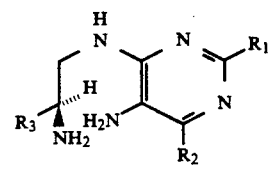

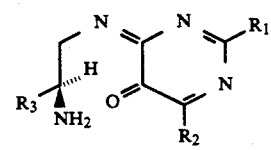

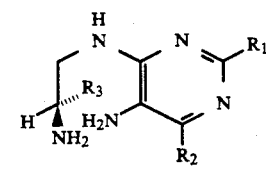

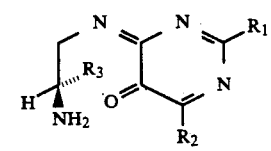

wherein $R_1$ and $R_2$ are the same or different and represent hydrogen, methyl, hydroxy, amino, alkyl or dialkylamino, alkoxy, benzyloxy, or benzylthio; $R_3$ represents an alkene, alkyne, cycloalkyl, benzyl, alkyl (substituted with hydroxy, acetoxy, benzyloxy, alkoxy, alkylthio, amino, carboxy, oxo, or phosphate), a protected aldehyde, or

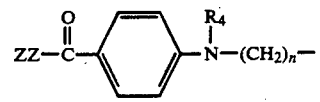

wherein n=1 or 2, $R_4$ is hydrogen, formyl, methyl, or propargyl, and ZZ represents an amino acid or amino acid polymer. Also, a process for tetrahydropteridine N5-formylation for the preparation of, for example, N5-formyl-(6S)-tetrahydrofolic acid.

4 Claims, No Drawings

PROCESS FOR N5-FORMYLATING TETRAHYDROPTERIDINES

FIELD OF THE INVENTION

The present invention relates to intermediates and a process for the preparation of tetrahydropteridine C6-stereoisomers.

BACKGROUND-DISCUSSION OF PRIOR ART

There is a great need for tetrahydropteridine C6-stereoisomers. For example, N5-formyl-tetrahydrofolic acid (also known as leucovorin) is being used to potentiate the effects of 5-fluoro-uracil in the treatment of several forms of cancer. Another use is the regime of leucovorin "rescue" following high dose methotrexate in cancer chemotherapy or for immunosuppression. Leucovorin is also co-administered with trimetrexate for the treatment of Pneumocystis carinii pneumonia which is common in AIDS patients. Megaloblastic anemia and dihydropteridine reductase deficiency are also treated with leucovorin. Yet because of the unavailability of the natural (6S)-isomer, these therapies have been performed with (6R,S)-N5-formyl-tetrahydrofolic acid. The unnatural (6R)-isomer cannot perform the functions of the natural isomer. Furthermore, the unnatural isomer of N5-formyl-tetrahydrofolic acid is cleared much more slowly from the blood. Several hours after administration the concentration of unnatural isomer can exceed that of the natural isomer by two orders-of-magnitude. Enzymes, such as thymidylate synthase and glycinamide ribonucleotide formyl transferase, are inhibited by the unnatural isomers of their tetrahydrofolate cofactors. Further, it is well known that high concentrations of folates can cause kidney damage.

Another natural tetrahydropteridine, (6R)-tetrahydrobiopterin ((6R)—$BH_4$) is required for metabolic control of phenylalanine levels, and for the biosynthesis of serotonin and the catecholamine neurotransmitters/hormones. In these roles it functions as the natural cofactor for the three aromatic amino acid hydroxylases. Recently (6R)—$BH_4$ has been found to be important in the regulation of blood pressure and in the immune response as a participant in the formation of nitric oxide from arginine. The importance of the C6-chirality of $BH_4$ for its biological activity has been well demonstrated. Cofactor replacement therapy for children having a defect in the tetrahydrobiopterin biosynthetic pathway now uses exclusively the costly natural (6R)-isomer. There are several other non-therapeutic uses for specific C6-stereoisomers of tetrahydropteridines, for example as affinity ligangs for enzyme purification. Pure unnatural isomers of tetrahydropteridines are also required for experimental elucidation of their mechanism of toxicity.

Since prior to this invention there has been no method for the synthesis of important tetrahydropteridine C6-stereoisomers, other approaches have been used for their production, but with limited success. Oxidized pteridines have been reduced with chiral reagents but this gives only a low enantiomeric excess. The natural isomers of tetrahydrofolic acid and tetrahydrobiopterin have been produced by enzymatic reduction of their respective 7,8-dihydropterins with dihydrofolate reductase, but this is useful only for small quantities. The enantiomers of 6methyl-tetrahydropterin have been resolved by fractional crystallization as the tartrate salt. Tetrahydrofolic acid (as a methylchloroformate derivative), leucovorin, and pentacetyl-tetrahydrobiopterin, all of which are diastereomers, also have been resolved by fractional crystallization. These methods suffer considerable loss of yield either in the multiple crystallizations required to reach acceptable enantiomeric purity and/or in the subsequent chemical steps needed to liberate the desired product from a derivative. Tetrahydrobiopterin, 5,10-methylenetetrahydrofolic acid and leucovorin have been chromatographically separated into individuaL C6-isomers. However, this approach is very limited with respect to scale. Considering the deficiencies of all the reported methods in filling such an important need, it is evident that there existed no obvious synthesis for 6-monosubstituted tetrahydropteridine C6-stereoisomers.

This invention was made in part with Government support under NS-26662 awarded by the National Institute of Neurological Disorders and Stroke and GM-30368 awarded by the National Institute of General Medical Sciences. The Government has certain rights in the invention.

SUMMARY OF THE INVENTION

Accordingly, it is an object of this invention to provide chiral intermediates for the C6-stereospecific synthesis of 6-monosubstituted tetrahydropteridines.

A further object of this invention is to provide a method for the C6-stereospecific synthesis of 6-monosubstituted tetrahydropteridines with the advantages of:

a) use of either naturally occurring chiral compounds, or known methods of asymmetric synthesis for generation of chiral starting materials;
b) use of inexpensive starting materials;
c) convenient implementation on a large scale;
d) production of substantially pure C6-enantiomers of tetrahydropteridines in good yield;
e) general applicability to tetrahydropteridines related to both tetrahydrofolic acid and tetrahydrobiopterin;.
f) capability for generation of either 6R or 6S isomers.

Unexpectedly, the inventors have found that pyrimidine derivatives of the following formula serve as intermediates to 6-monosubstituted tetrahydropteridine C6-stereoisomers:

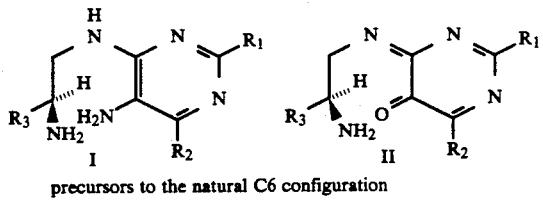

precursors to the natural C6 configuration

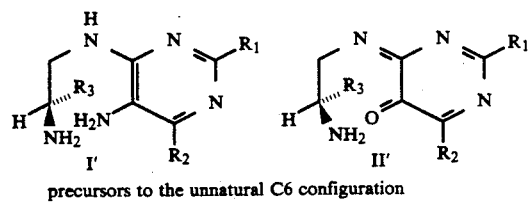

precursors to the unnatural C6 configuration wherein $R_1$ and $R_2$ are the same or different and represent hydrogen, methyl, amino, $C_1$-$C_4$ alkyl or dialkylamino, hydroxy, $C_1$-$C_6$ alkoxy, benzyloxy, or benzylthio with the proviso that both $R_1$ and $R_2$ cannot both be hydrogen; $R_3$ represents (1) alkyl of 1 to 6 carbons;
(2) alkene of 2 to 4 carbons;
(3) alkyne of 2 to 4 carbons;
(4) cycloalkyl, saturated or unsaturated, of 3 to 7 carbons with 3 to 7 carbons in the ring;
(5) benzyl, thienylmethyl, furylmethyl, or pyridylmethyl;
(6) alkyl of 1 to 6 carbons, substituted with 1, 2, or 3 of hydroxy, acetoxy, benzyloxy, methoxy, ethoxy, methylthio, ethylthio, or benzylthio;
(7) alkyl of 1 to 6 carbons, substituted with 1 of amino, carboxy, oxo, or phosphate, and 0, 1, or 2 of hydroxy, acetoxy, or benzyloxy;
(8)

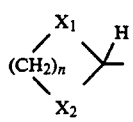

wherein $X_1$ and $X_2$ are the same or different and represent —O— or —S—, and n=2 or 3;
(9)

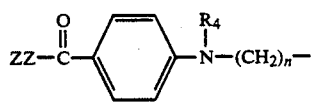

wherein $R_4$ represents hydrogen, formyl, or an alkyl, alkenyl, or alkynyl of 1-3 carbons, n=1 or 2, and ZZ is Z or represents the residue of an amino acid or amino acid polymer of the formula

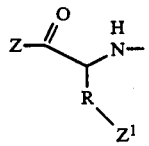

wherein Z represents OH, $C_1$–$C_4$ alkoxy, or $NH_2$, R represents a divalent alkyl radical of 1 to 5 carbons, and $Z^1$ represents $NH_2$ or $COZ^2$ where $Z^2$ is Z or the residue of an amino acid or amino acid polymer of the formula

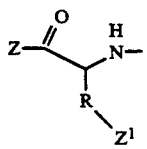

where the total number of amino acid residues in ZZ does not exceed 7 and each Z, R, $Z^1$, and $Z^2$ operates independently in defining ZZ.

A further object of this invention is to provide a method for the conversion of tetrahydropteridines to N5-formyl derivatives having the advantages of (a) good yield, (b) fast reaction times, (c) applicability to the regiospecific N5-formylation of tetrahydrofolic acid and its derivatives to provide N5-formyl-tetrahydrofolic acid and its derivatives, (d) a low total cost of reaction, and (e) maintenance of the enantiomeric purity of the starting tetrahydropteridine. This process comprises the use of N-formylimidazole, or a mixture of 1,1'-carbonyl-diimidazole and formic acid.

Further objects and advantages of this invention will be apparent from the description which follows.

DESCRIPTION OF THE INVENTION

Synthesis of Intermediates I and I'

The intermediates of this invention (I) (which is precursor to a naturally C6-configured tetrahydropteridine) or (I') (precursor to an unnaturally configured tetrahydropteridine) can be generated by a number of different routes, one of which is illustrated. A 2-monosubstituted ethanediamine (III) or (III') which is substantially stereochemically pure at C2 and in which the 2-amino group is protected is condensed with a 4-chloro-5-nitro-pyrimidine (IV) to produce (V'), respectively:

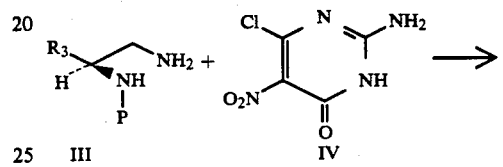

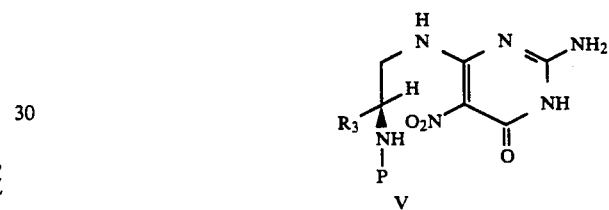

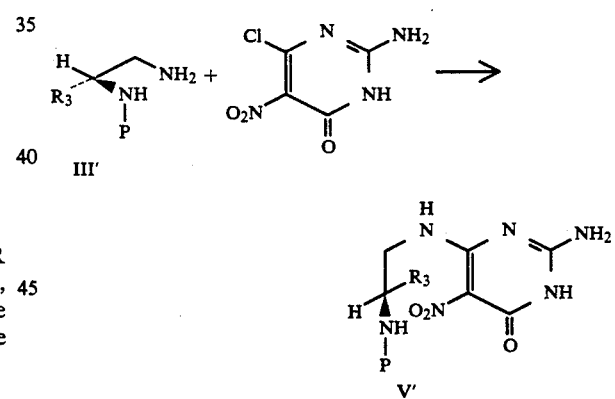

Many pyrimidines having the structure of (IV), where $R_1$ and $R_2$=hydrogen, hydroxy, amino, alkylamino, alkoxy, benzylthio, or benzyloxy have been synthesized, or are available commercially. This condensation is performed by procedures known to the art. These condensations are typically performed in an alcohol solvent, typically ethanol. A base such as a bicarbonate or a carbonate salt, or more typically, a hindered amine is included to facilitate completion by neutralization of the acid in the reaction. An important factor in this condensation with respect to the current invention is that the salt of the hindered amine base, for example $[Et_3NH^+]Cl^-$, frequently coprecipitates with the desired product. If this contaminant is not removed, for example by washing product with water, extraction of product into organic solvent, recrystallization, or chromatographically, etc., it can interfere with the subsequent cyclization of (I) or (I').

Intermediates (I) or (I') are prepared by methods other than by condensation of a protected diamine (III), or its enantiomer (III') with the chloro-nitro-pyrimidine (IV). For example, the protected diamine (III) or (III') can be condensed with a 4,6-dichloropyrimidine. The remaining chlorine is displaced by nucleophilic substitution to introduce $R_2$, the 5-position nitrosated, and this nitroso group reduced to give (I) or (I'), respectively. It should be understood, therefore, that the process of this invention is not limited to the condensation of a protected diamine (III) or (III') with a chloro-nitro-pyrimidine IV, although this is a preferred method of preparing intermediate (I) or (I').

Protected diamines (I) or (I') have been synthesized from optically active amino acids. Since many methods are available for the preparation of enantiomers of unusual amino acids, this route is not limited to the use of natural amino acids or their isomers. Another example of the preparation of diamines (III) or (III') is via asymmetric Strecker condensation of an aldehyde with a chiral amine and cyanide, followed by reduction of the resulting optically active amino-nitrile.

There are a number of amine protecting groups P suitable for diamines (III) or (III') in the preparation of intermediates (I), (I'), (II), or (II'). A protected diamine provides a regiospecific condensation. An unprotected diamine (P=H) can be used for the reaction, but can give as much as 15% contamination due to reaction of the free 2-amino group. This by-product, which is difficult to remove, will ultimately lead to an undesired 7-monosubstituted pteridine in the final product. In the context of the condensation reaction, any standardly used protecting group, such as t-butyloxycarbonyl, benzyloxycarbonyl, benzyl, α-methylbenzyl, etc., will produce a regiospecificity of greater than 99%. However, this protecting group must be removed prior to the cyclization described below. Intermediates (II) or (II') will not cyclize to give an acceptable yield of tetrahydropteridine if this protecting group is left in place. The point at which the protecting group P is cleaved after condensation with (IV) is used to optimize the intervening reactions as will become evident.

The inventors have also developed a method for converting an α-amino acid enantiomer into a suitably protected diamine (III) or (III'). An α-amino amide is prepared from an amino acid or amino acid ester by any of several well known methods. Protection of the α-amino group by, for example, benzyl or t-butyloxycarbonyl is then accomplished by known methods. In some cases (see Example 2) protection before amide formation is preferred. The α-protected amino-amide is then reduced to (III) or (III') by a borane reagent, preferably borane/THF or borane/dimethylsulfide. A simple series of extractions provides the desired protected diamine in good yield, and sufficiently free of other amine contaminants to allow condensation with the pyrimidine without further purification.

The use of the chloro-nitro-pyrimidine (IV) has the advantage that, with respect to the pyrimidine moiety, only reduction of the nitro group to the amine is required for conversion of (V) to (I) or (V') to (I'). A number of methods are available for the reduction, catalytic hydrogenation being preferred. This is usually carried out in aqueous or alcoholic solvent, but in the case of those compounds containing a group, such as p-amino-benzoyl-glutamate, addition of a cosolvent, such as dimethylformamide, gives higher yields by increasing solubility. For nitropyrimidines (V) or (V') containing groups, such as benzylthio, which may be prematurely cleaved by hydrogenation, dithionite is used. Catalytic hydrogenation serves also to conveniently cleave certain protecting groups P, such as benzyloxycarbonyl, benzyl, or α-methyl-benzyl, in the same reaction as the nitro group is reduced. Alternatively, an acid cleavable protecting group, such as t-butyloxycarbonyl, can be removed either after or before nitro group reduction. Modifications of $R_3$ in the nitropyrimidine (V) or (V') can also be performed prior to reduction of the nitro group. Thus the protecting group P is selected in part to optimize the modifications of $R_3$ prior to reduction of the nitro group. For those compounds where $R_3$ is not modified (see Example 1), a protecting group removed by catalytic hydrogenation is preferred. In some cases derivatization of the amino group protected by P with a second group facilitates modification of $R_3$ by, for example, providing increased solubility (see Example 2).

Intermediates (I) and (I') are labile to oxidation by air and, if stored, are kept under inert gas between 0° C. and −80° C. either as a hydrohalide salt or, if in solution, between pH 3 and pH 1. The catalysts used for reduction of the nitro group promote this air oxidation, and are rigorously removed subsequent to hydrogenation.

Cyclization and Reduction of Intermediate (II) or (II')

The cyclization of intermediate (II) or (II') to give, respectively, naturally (IX) or unnaturally (IX') C6-configured tetrahydropteridines as well as a method for obtaining these from intermediate (I) or (I'), respectively, is summarized below (only the natural isomer is illustrated).

An aqueous or partially aqueous solution of I, for example, is oxidized to a 5-imino quinoid pyrimidine (VI). The 5-imine is then hydrolyzed, a reaction catalyzed by acid, yielding a quinoid pyrimidine with a carbonyl group at position 5 (II). Cyclization of (II) then occurs, especially when neutralized, to give a quinoid dihydropteridine (VIII) via an intermediate C4a-hydroxy adduct (VII). The quinoid

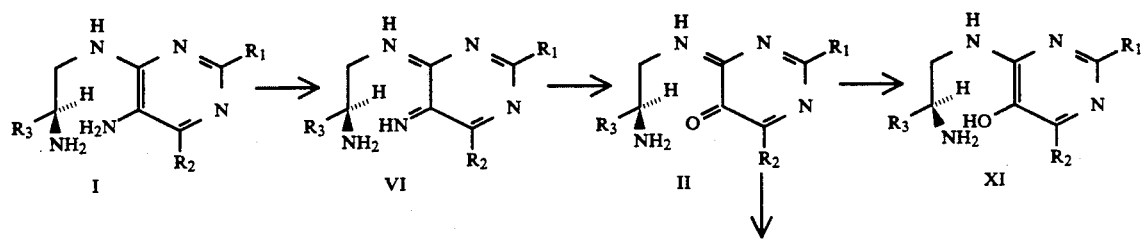

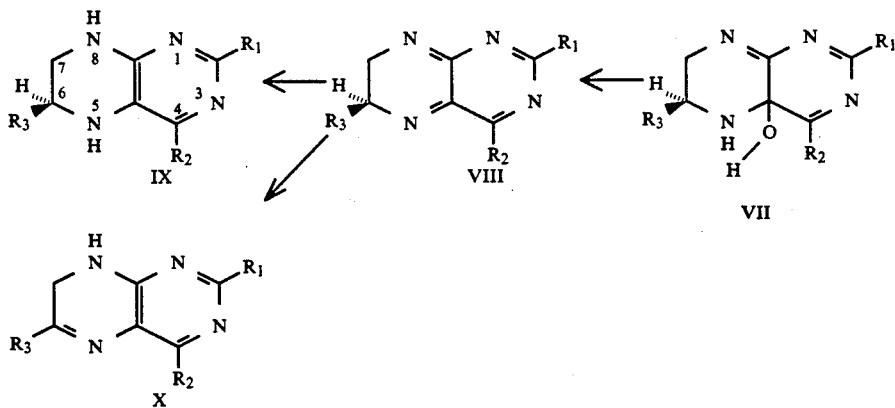

dihydropteridine is then reduced to give the desired 6-monosubstituted tetrahydropteridine (IX).

Unexpectedly it was found that by: (1) producing intermediate (II) or (II') of sufficient purity (2) using a mineral acid, such as HCl to catalyze hydrolysis of (VI) to (II), (3) keeping the concentration of intermediates (II), (VII) and (VIII) below 0.1M, preferably less than 0.025M, (4) cooling prior to neutralization of intermediate (II), (5) adjusting to between about pH 8 and 12 for the cyclization of (II) to (VII), (6) use of a reductant which rapidly reduces quinoid dihydropteridines (VIII), but not 7,8-dihydropteridines (X) to tetrahydropteridines (IX), and (7) precise timing of addition of the reductant to minimize by-product formation, 6-monosubstituted tetrahydropteridines could be synthesized, and also that chirality of the 6-position was retained.

Oxidation. A solution of intermediate (I) or (I') (only the former is illustrated) in a mixture of water and a miscible solvent, such as methanol or ethanol, is oxidized to the 5-imine (VI). An oxidant, for example bromine or iodine, is used which will rapidly form the 5-imine (VI), but which is relatively inert with respect to reaction with functionalities in the $R_3$ substituent. One mole of $Br_2$ or $I_2$/mole of (I) will eventually lead to the desired 5-imine (VI), although a 1.1 to 1.8-fold excess produces a more rapid oxidation. Since the half-potential of intermediate I or I' is about +0.1 Volt vs Ag/AgCl many mild oxidants are also suitable for this oxidation. Further, electrochemical oxidation at 0.1 Volt vs Ag/AgCl or higher, preferably about 0.3 Volt vs Ag/AgCl can be used instead, and has the advantage of selectivity and giving a more salt-free reaction.

Hydrolysis. Hydrolysis of (VI) to (II) is performed, between pH 0 and pH 3, preferably between pH 1 and 3, adjusted, if necessary, by a mineral acid, such as HCl. This acid can be added, if necessary, immediately after or, preferably, before oxidation. Typically, solutions of (I) or (I') are mildly acidic before oxidation for the purpose of optimal storage (see above). The use of either $Br_2$ or $I_2$ as oxidant generates HBr or HI, respectively, which act as appropriate acid catalysts. The optimal total acidity of the reaction immediately following oxidation is that which both promotes hydrolysis of the 5-imine (VI) and maximizes the stability of the resulting 5-keto-pyrimidine (II). Hydrolysis of the 5-imine (VI) to 5-keto-pyrimidine (II) is typically complete between 2 and 10 minutes at room temperature, or longer if cold. Spectral and $H_2O^{18}$ exchange studies suggest that the 5-keto-pyrimidine (II or II') is in equilibrium with a hydrated form.

Cyclization. A chirality maintaining cyclization of a solution of 5-keto-pyrimidine (II) which is formed from the 5-imino-pyrimidine (VI) (or from other precursors), and which is substantially purified from tautomerization promoting impurities, to quinoid dihydropteridine (VIII) is initiated by adjustment of pH, preferably at low temperature. After completion of hydrolysis as described above, the reaction is cooled to less than 5° C., between 0° C. and solvent freezing point being preferred. The optimal pH for cyclization is between pH 8 and 12. A base which does not significantly promote general catalysis of tautomerization of quinoid dihydropteridine (VIII) to 7,8-dihydropteridine (X), such as an alkali or alkaline-earth hydroxide, for example sodium hydroxide, is preferred for obtaining this pH. If adjustment of pH is done slowly at room temperature or above, a poor yield results due to nonoptimal cyclization during the titration itself. The lower temperature allows enough time for completion of the titration before significant cyclization has occurred. The concentration of the intermediates during cyclization of (II) are kept below 0.1M, preferably less than 0.025M (this is especially important when $R_3$ contains acidic or basic functionalities, such as in the synthesis of tetrahydrofolic acid and its analogs). When II or II' are generated from the 5-amino-pyrimidine I or I', respectively, purification from tautomerization promoting impurities is conveniently performed pior to the reduction that generates the 5-amino group.

Reduction. Unexpectedly, it was found that when quinoid 6-monosubstituted dihydropteridines (VIII) are produced in the above described manner, tetrahydropteridine C6-stereoisomers (IX) could be obtained by a chirality maintaining reduction which entails precise timing of the addition of certain reductants. If subsequent to neutralization, too short a reaction time is given to complete the cyclization of (II), addition of reductant produces an undesirable divicine derivative (XI). Conversely, if reductant is added at too long a time after neutralization, tautomerization of quinoid dihydropteridine (VIII) to 7,8-dihydropteridine (X) occurs. The preferred time after pH adjustment when reductant is added is between 0.5 min to 10 min at 4° C., or longer at lower temperatures.

Catalytic hydrogenation is generally too slow to produce an optimal timing of reduction. Further, this method can reduce 7,8-dihydropteridines (X) to racemic tetrahydropteridines, thus degrading the enantiomeric purity of the desired product (IX). Thiol reagents, such as 2-mercaptoethanol, can be used, but this places an extra constraint on optimal timing of its addition. If a thiol reagent is used, it must be added not only after cyclization of 5-keto-pyrimidine (II), but also after dehydration of the intermediate adduct (VII) to quinoid dihydropteridine (VIII). Although a thiol reagent can be used, an agent such as a dithionite salt, for example $Na_2S_2O_4$, or ascorbic acid is preferred. Any 7,8-dihydropteridine which may have formed is not reduced by ascorbic acid or by dithionite at subambient temperature. The tetrahydropteridine C6-stereoisomer (IX) is purified from the final reaction mixture by methods well known to those skilled in the art.

The process described above is performed on a wide range of scale using traditional laboratory equipment. Very large cyclization reactions can benefit from the use of a flow reactor, as is common in industrial practice. This facilitates the combining of the solution of 5-imine (VI) with the titrant base in a flowing stream. The mixture is subsequently combined with the reductant. The more accurate timing of reagent addition by this method decreases the need for large changes of reaction temperature.

Methods for determining the enantiomeric purity of the 6-monosubstituted tetrahydropteridine products resulting from cyclization of (I), (I'), (II), or (II') have been established (see Examples I Ia II, and IIa). These have shown that chiral purities in excess of 97% are consistently obtained. The synthesis of (6R)-propyl-tetrahydropterin and (6S)-propyl-tetrahydropterin from D and L-norvaline, respectively, consistently gave greater than 99% enantiomeric purity.

Formylation of N5 of Tetrahydropteridines

N-Formyl-imidazole and related derivatives such as N-formyl-benzimidazole have been used to formylate simple monoamine compounds. However, since tetrahydrofolic acid contains several amine groups which can be formylated, it is not obvious that the use of this reagent would selectively generate a significant amount of the desired N5-formyl-tetrahydrofolic acid. Neither is it clear that a reaction involving N-formylimidazole would proceed without racemization of tetrahydropteridine 6-position chirality. The inventors have discovered a method that accomplishes a highly regiospecific formylation of N5 in a tetrahydropteridine, for example (6S)-tetrahydrofolic acid, leaving the original enantiomeric purity unchanged. The method comprises dissolving the tetrahydropteridine in a solvent, preferably under inert atmosphere. The solvent should provide good solubility for the tetrahydropteridine and be unreactive toward the N-formyl-imidazole, for example, N,N-dimethyl-formamide. The solvent should be substantially dry. N-Formyl-imidazole is added with stirring. The reaction can be performed between 0° C. and 50° C., conveniently at ambient temperature. An excess of reagent is generally required, typically between 1.5 and 3 moles per mole of tetrahydropteridine, being dependent, in part, on the presence of residual water or other protic solvents in the reaction. The optimal amount can be determined by monitoring the conversion of tetrahydropteridine by HPLC.

Alternatively, 1,1'-carbonyl-diimidazole (CDI) and formic acid can be used instead of N-formyl-imidazole. Tetrahydropteridine is dissolved in solvent, selected as discussed above, under inert atmosphere, and formic acid, preferably of 98% or greater purity, added. A molar ratio of between 1.5 to 10, preferably 2 to 5, formic acid to tetrahydropteridine is used (although certain reactions benefit from higher formic acid, see below). CDI is added all at once or in portions in a molar ratio totaling 1.5 to 3 per mole tetrahydropteridine. The inventors believe that this reaction proceeds via in-situ formation of N-formyl-imidazole, although they do not wish to be bound by this. The reaction is complete within 10 minutes at ambient temperature. Product can be purified from the reaction by precipitation with a solvent in which imidazole is soluble, but which is a poor solvent for the N5-formyl-tetrahydropteridine, for example an ether, conveniently ethyl ether.

Either of the above methods, but preferably CDI plus formic acid, can also be used to N5-formylate the tetrahydrofolic acid in a crude reaction mixture obtained from cyclization of intermediate (II) or (II'). However, in some cases, for example with tetrahydrofolic acid, a somewhat higher amount of formic acid, preferably in the range of 1% to 5% v/v solvent, promotes homogeneous solution of the tetrahydropteridine and the reaction salts. Preparation of N5-formyl-(6S)-tetrahydrofolic acid by this procedure results in no detectable racemization.

EXAMPLES

General Procedures

Unless otherwise specified, all pH values of primarily nonaqueous solutions were measured after 10-fold dilution in water. THF was dried by distillation from LiAlH; $CH_2Cl_2$ and DMF were dried over 4A sieves. Solvents were removed using a rotary evaporator with a room temperature bath and vacuum pump, and products were dried under high vacuum over $P_2O_5$. Glass fiber pads (~1.5μ particle retention) were used for general filtration, and especially to remove catalyst from XVIa and XVIb. $^1H$ and $^{13}C$ NMR spectra were acquired in $DMSO_{d6}$ at 300 MHz and 75 MHz, respectively, unless otherwise specified. Ultraviolet extinction coefficients ($\epsilon$) are in units of $M^{-1}$ $cm^{-1}$. Norvalinamide.HCl was obtained by the method of Smith and Polglase, J. Biol. Chem. 180, 1209 (1949) further recrystallized from water/acetone. 2-Amino-6-chloro-5-nitro-4(3H)-pyrimidinone was prepared by the method of Bailey and Ayling, Biochemistry 22, 1790 (1983) (solutions of aged material should be filtered if necessary to remove decomposed pyrimidine). 1,1,1-Tris(acetoxy)-1,1-dihydro-1,2-benziodoxol-3(1H)-one was prepared as described by Dess and Martin J. Org. Chem., 48, 4155 (1983).

Example 1: Synthesis of (6S)-Propyl-tetrahydropterin

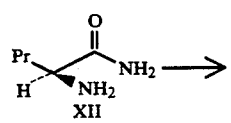

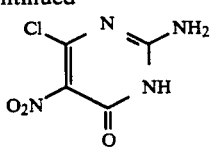

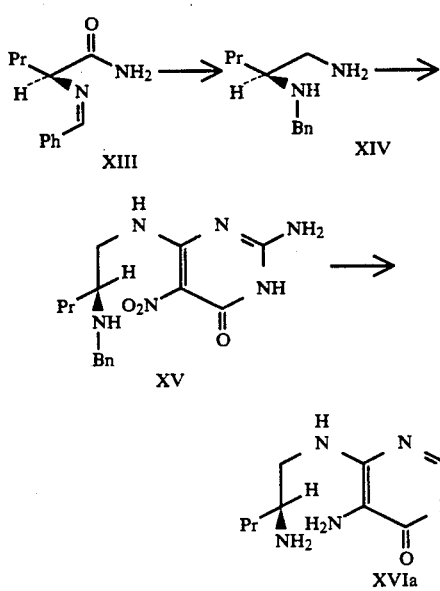

1-Amino-(2S)-benzylamino-pentane (XIV). Fresh benzaldehyde (4.02 g, 37.9 mmol) was added to a slurry of 4.0 g L-norvalinamide.HCl (XII) (26.2 mmol) in 70 mL 1-PrOH, followed by 4.08 mL Et₃N (29.3 mmol). The mixture, which became clear after stirring at 23° C. for 70 minutes, was then evaporated to 15 mL, and 175 mL Et₂O added. After filtration, the precipitated salts were washed with additional Et₂O, solvent evaporated from the combined filtrate, and residual benzaldehyde removed under high vacuum to give 5.13 g N-benzylidene-L-norvalinamide (XIII) as a light yellow solid (UV $\lambda_{max}$=249 nm in MeOH). The purity of this material was determined by normal phase HPLC.

All of the Schiff's base XIII was dissolved in 120 mL dry THF, heated, and 15.2 mL 10.1M borane-Me₂S (154 mmol) added with stirring over 20 min while simultaneously distilling off Me₂S. The reaction was then refluxed another 2.5 h, cooled to ambient temperature, and acidified to pH 4 with HCl$_{conc}$. After extraction once with 250 mL Et₂O, the aqueous phase was taken to pH 11 with solid NaOH, and extracted with 4×150 mL Et₂O. The latter extract was concentrated, and dried to give 3.09 g thick oil containing 11.0 mmol XIV (42%). Analysis of this material by ion pair HPLC showed 93% of the absorbance area in the product peak. A sample was purified as the dihydrochloride salt by repeated crystallization from MeOH/Et₂O to give a white, highly hygroscopic semi-solid: ¹H NMR δ 0.89 (t, 3 H, CH₃), 1.37 (m, 2 H, —CH₂—CH₃), 1.80 (m, 2 H, —CH—CH₂—), 3.2–3.55 (m, 3 H, —CH₂—NH₂, CH—NH), 4.26 (m, 2 H, benzyl). 7.4–7.7 (m, 5 H, Ar); ¹³C NMR δ 13.5, 17.9, 29.2, 38.2, 47.3, 55.0, 128.4, 128.8, 130.2, 131.6; HRMS (+FAB, Xe, thioglycerol) m/z calcd for C₁₂H₂₁N₂(MH+) 193.170, found 193.171.

2-Amino-6-[((2'S)-Benzylamino-pentyl)amino]-5-nitro-4(3H)-pyrimidinone (XV). 2-Amino-6-chloro-5-nitro-4(3H)-pyrimidinone.H₂SO₄ (3.7 g, 12.8 mmol) was dissolved in 250 mL hot EtOH$_{abs}$, adjusted to pH 9.5 with Et₃N, taken to reflux, and 3.09 g XIV (containing 11.0 mmol) added. After 90 min stirring, analysis by ion pair HPLC indicated complete consumption of diamine. Half of the solvent was distilled off, and the mixture cooled to ambient temperature. A first crop was collected by filtration, washed with a few mL cold EtOH, and dried to give 4.04 g light yellow powder containing 9.46 mmol XV. Another 0.082 mmol was found in the filtrate (93% total), from which 0.046 mmol (86% recovered) was collected after cooling to −20° C. Greater than 98% of the 340 nm chromatographic absorbance resided in the product peak.

A sample was purified to a white powder by extraction into, and crystallization from, CHCl₃: UV(λmax) (0.1M HCl) 236 nm (ε=12,800), 334 (ε=13,500); (0.1M NaOH) 235 (sh), 348 (ε=14,800); ¹H NMR δ 0.93 (t, 3 H,—CH₃), 1.35-1.57 (m, 4 H,—CH₂CH₂—), 2.78 (m, 1 H,—NH—), 3.2-3.7 (m, 4 H,—CHCH₂N—,—NH—), 3.84 (m, 2 H, benzyl), 7.25-7.5 (m, 5 H, Ar); ¹³C NMR δ 14.1, 18.5, 33.9, 43.2, 49.6, 54.6, 110.4, 126.5, 127.9, 128.0, 140.7, 154.2, 156.6, 159.0; HRMS (+FAB, Xe, thioglycerol) m/z calcd for C₁₆H₂₃N₆O₃(MH+) 347.183, found 347.177; Anal. Calcd for C₁₆H₂₂N₆O₃: C, 55.32; H, 6.67; N, 24.19. Found: C, 55.30; H, 6.64; N, 24.08.

6-[((2S)-Amino-pentyl)amino]-2,5-diamino-4(3H)-pyrimidinone (XVIa). To a suspension of 2.02 g crude XV (containing 4.73 mmol) in 200 mL MeOH was added 2.0 g 5% Pd/BaSO₄, and the mixture stirred vigorously at room temperature under 45 psi hydrogen. Analysis by cation exchange HPLC showed complete reduction of the nitro group and debenzylation by 24 h. With the reaction still under an atmosphere of H₂, the mixture was pulled through an in-line filter using reduced pressure into an ice-cooled flask. Deaerated fresh MeOH (50 mL) was added to the hydrogenation vessel and pulled through the filter to wash remaining product from the catalyst. The clear light yellow filtrate was quickly sparged with argon, adjusted to pH 2 with 5M HCl in MeOH, and concentrated to 60 mL. Analysis of this material by HPLC showed 3.60 mmol XVIa (76%) with 92% of the total 270 nm absorbance area in the product peak, and no significant electrochemically active impurities. A sample was purified by addition of 98% H₂SO₄ and precipitation with Et₂O. After washing with fresh Et₂O and drying, a white powder was obtained that showed greater than 99% of the 270 nm chromatographic absorbance in a single peak. An extinction coefficient was determined by dichlorophenol indophenol (DCIP) titration: UV(λmax) (0.1N HCl) 217 nm (ε=30,200), 270 nm (ε=15,600); HRMS (+FAB, Xe, thioglycerol) m/z calcd for C₉H₁₉N₆O(MH+) 227.162, found 227.161.

(6S)-Propyl-5,6,7,8-Tetrahydropterin (XXIIa). A solution of crude XVIa (1.50 mmol) in 25 mL MeOH was diluted with 25 mL of water, well sparged with argon, warmed to 27° C., and 54 mL 50 mM I₂ in MeOH (2.7 mmol) added all at once with vigorous stirring. After 12 min the mixture was cooled on ice over 7 min to 4° C., and rapidly (<20 sec) adjusted to pH 10 with 10M NaOH. After 1.0 min, 6.0 mL ascorbic acid (0.75M in ice-cold water, 4.5 mmol) was added quickly with good stirring and continued bubbling with argon. Analysis after 5 min by cation exchange HPLC showed 0.97 mmol product (65%) along with traces of 6-propyl-7,8-dihydropterin (XXIIIa) and XIXa (λ$_{max}$=285, pH 3.3.

After acidification to pH 3.0 with 6N HCl and addition of 78 μL 2-mercaptoethanol (1.11 mmol), the reaction was evaporated to approximately 8 mL.

Crude product was purified by preparative cation exchange chromatography. The fractions not containing significant 6-propyl-7,8-dihydropterin typically gave 89% recovery of XXIIa. Analytically pure colorless material was obtained by two crystallizations from 0.25M H$_2$SO$_4$/ACN: UV($\lambda_{max}$) (0.1M HCl) 215 nm ($\epsilon$=16,000), 265 nm ($\epsilon$=14,900); $^1$H NMR (D$_2$O, TSP=0 ppm) δ 0.95 (t, 3 H, CH$_3$), 1.48 (m, 2 H, CH$_2$), 1.75 (m, 2 H, CH$_2$), 3.35 (q, 1 H, H$_{7a}$), 3.59 (m, 1 H, H$_6$), 3.75 (q, 1 H, H$_{7b}$); ($^{13}$C NMR (D$_2$O, TSP=0 ppm) δ 16.0, 21.0, 34.0, 44.2, 54.8, 88.0, 155.4, 155.9, 161.1; HRMS (+FAB, Xe, thiogylcerol) m/z calcd for C$_9$H$_{16}$N$_5$O(MH+) 210.135, found 210.139; Anal. Calcd for C$_9$H$_{15}$N$_5$O.H$_2$SO$_4$.½H$_2$O: C,34.17; H,5.74; N,22.14; S,10.13. Found: C,34.29; H,5.47; N,22.11; S,10.24.

Enantiomeric purity was determined by derivatization of 2 mg XXIIa.H$_2$SO$_4$ in 200 μL ACN with 60 μL phenylisothiocyanate (PTIC) (0.5 mmol) and 27 μL Et$_3$N (0.2 mmol). After 15 min at room temperature, 50 μL of the mixture was purified by reverse phase HPLC. The PTIC derivative was collected, and analyzed on a chiral HPLC column giving good resolution of the two C6-enantiomers (R$_s$=1.8) which showed enantiomeric purity of the product to be greater than 99%.

Example 1a: Synthesis of (6R)-Propyl-tetrahydropterin

The above series of reactions were repeated starting with D-norvaline with similar results, yielding (6R)-Propyl-tetrahydropterin having 99% enantiomeric purity.

Example 2: Synthesis of the Natural (6S)-Enantiomer of Tetrahydrofolic Acid

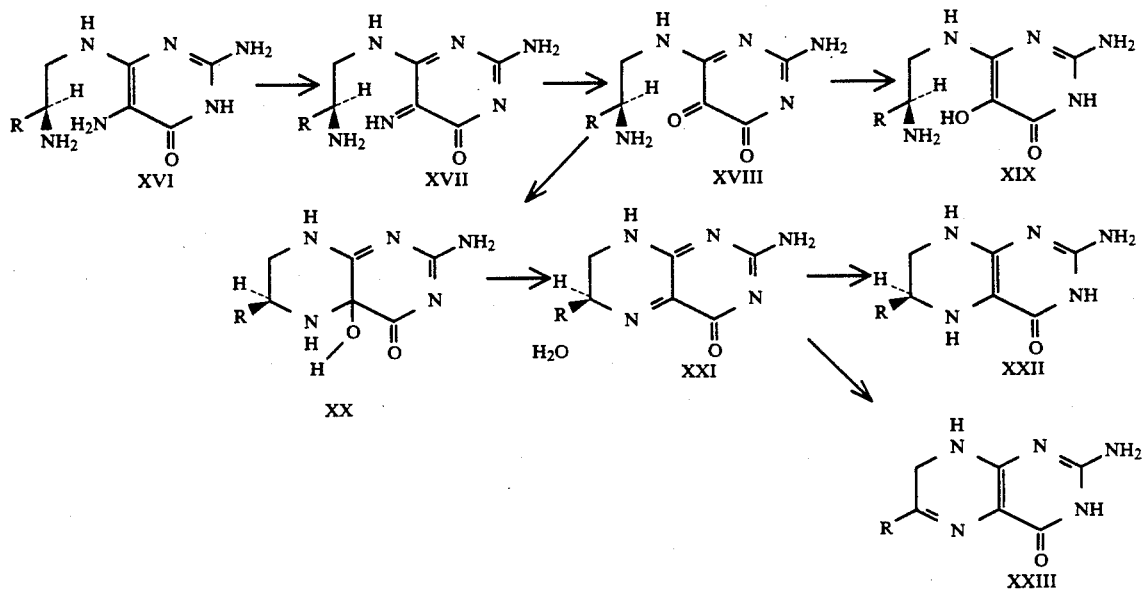

(a) R = CH$_3$CH$_2$CH$_2$

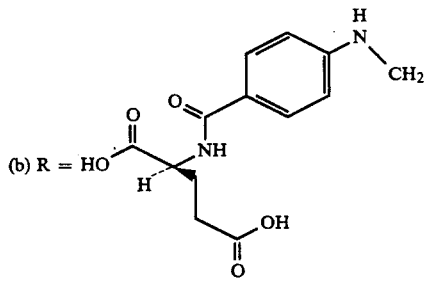

(b) R =

N-Benzyl-L-serine methyl ester hydrochloride (XXV). A solution of 20 g (0.129 mol) L-serine methyl ester hydrochloride (XXIV) in 100 mL MeOH was adjusted to pH 8 with 12.9 mL 10M NaOH thus precipitating NaCl. Benzaldehyde (15.0 g, 0.141 mol) was added and stirred well for 30 min. After cooling to 4° C., 2.43 g (0.064 mol) NaBH$_4$ was added in parts over one hour. The reaction was then warmed to ambient temperature and stirred for another hour. Analysis by ion pair HPLC showed that aside from the desired product, identified by co-elution with material obtained by esterification of N-benzyl-L-serine, the only other product observed was benzyl alcohol. The reaction was filtered, concentrated, and dried. The thick residue was dissolved in 120 mL acetone, refiltered to remove more salt, adjusted to between pH 1 to 1.5 with HCL gas, 750 mL Et$_2$O added, product collected by centrifugation, and dried, giving 28.1 g colorless hygroscopic solid. Chromatographic comparison to purified material showed this to contain 91.6 mmol (71%). MS (E.I., direct insertion) m/z(% relative abundance) 210(MH+)(5), 178(55), 150(64), 118(6), 106(29), 91(100); HRMS (+DCI, CH$_4$) m/z calcd for C$_{11}$H$_{16}$NO$_3$(MH+) 210.113, found 210.112.

N-Benzyl-L-serinamide (XXVI). N-Benzyl-L-serine methyl ester hydrochloride (XXV)(28.1 g, 80% pure, 91.5 mmol) was dissolved in 450 mL MeOH saturated with NH$_3$ at 0° C. The solution was then kept at room temperature in a pressure bottle. The flask was resaturated with NH$_3$ at 2 day intervals. Analysis by ion pair HPLC indicated 86% conversion to product after 6 days, at which time solvent was removed, and product dried. The resulting 29.0 g, crude material was extracted into 500 mL ethyl acetate/MeOH (3:2), filtered, and concentrated to a gum. This was re-extracted with 200 mL of 1-PrOH, 50 mL ethyl acetate added, and the suspension centrifuged. Removing the solvent from the supernate and drying gave 24.3 g thick oil of the hydrochloride salt (containing 74 mmol XXVI, 81%). A sample was purified by crystallization from MeOH-/acetone/(Et)$_2$O: $^1$H NMR δ 3.70 (m, 1 H, CH—CH$_2$), 3.87 (m, 2 H, —CH$_2$—), 4.15 (s, 2 H, benzyl), 5.58 (br s, 1 H, OH), 7.3–7.6 (m, 5 H, Ar), 7.67 (s, 1 H, CONH$_a$), 8.03 (s, 1 H, CONH$_b$); MS (E.I., direct insertion) m/z (% relative abundance) 195 (MH+)(2), 163(7), 150(51), 106(17), 91(100); HRMS (+DCI, CH$_4$) m/z calcd for C$_{10}$H$_{15}$N$_2$O$_2$(MH+) 195.113, found 195.113.

3-Amino-(2R)-benzylamino-propan-1-ol (XXVII). N-Benzyl-L-serinamide.HCl (XXVI) (45.7 mmol, 15.0 g of crude material) was mostly dissolved in 800 mL of dry THF under argon. The mixture was heated, and 46 mL 10.1M borane-Me$_2$S (0.465 mol) was added via syringe with stirring over 20 min and simultaneous distillation of Me$_2$S/THF, and then refluxed for 2 h. After cooling to room temperature, 11 mL of 6N HCL was added dropwise to give pH 4.5 to 5.0, and the reaction stirred for 30 min. Water was added to produce a clear solution which was extracted once with 300 mL Et$_2$O. The aqueous layer was adjusted to pH 12 with solid NaOH, product extracted with 3.8 L Et$_2$O, and the extract dried (Na$_2$SO$_4$). After removing solvent, drying under vacuum over NaOH pellets gave an oil weighing 8.35 g found by ion pair HPLC to

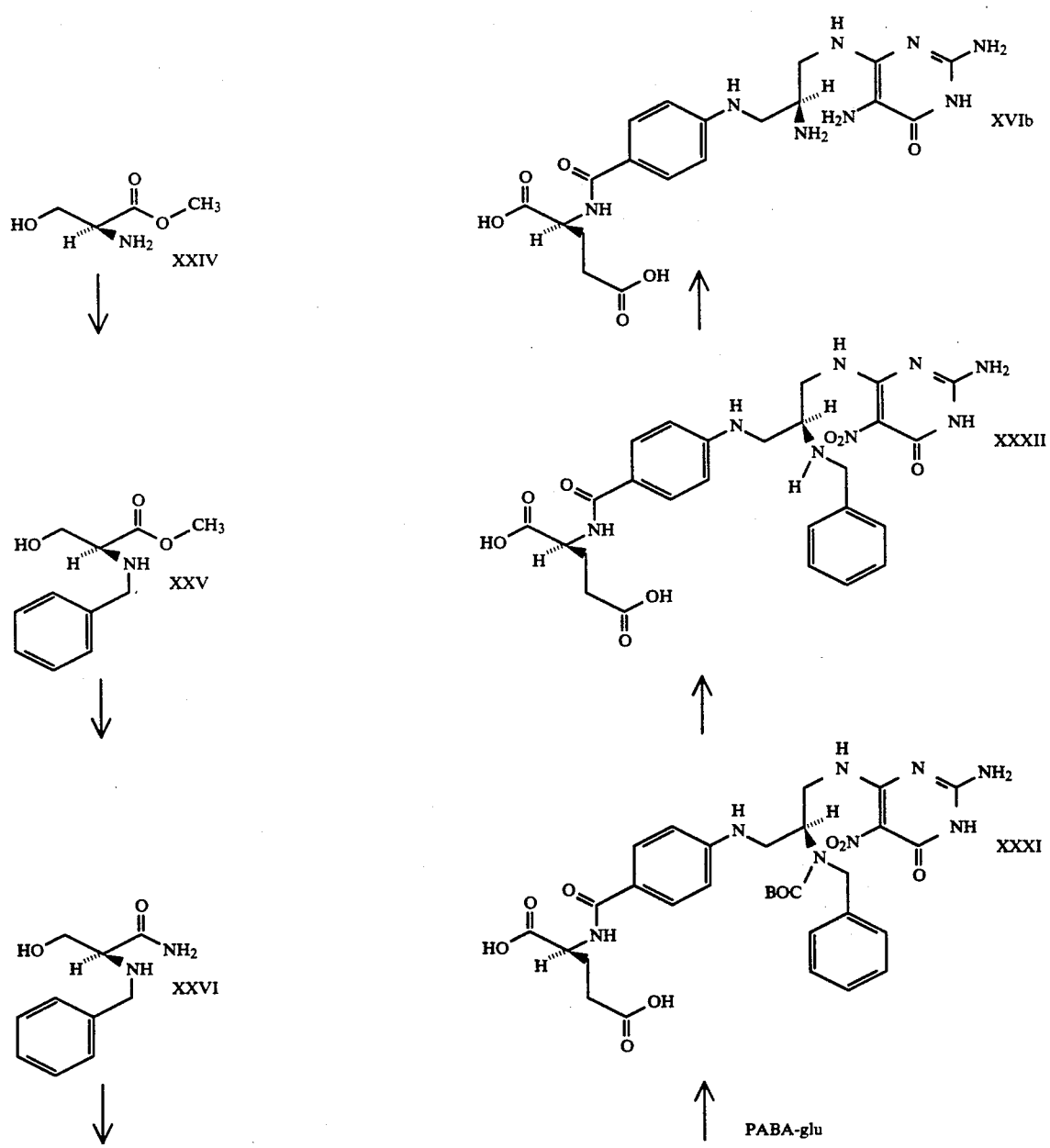

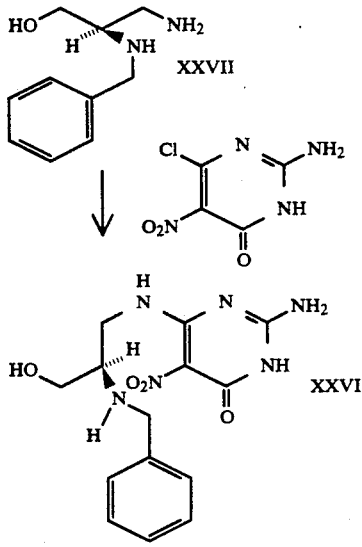
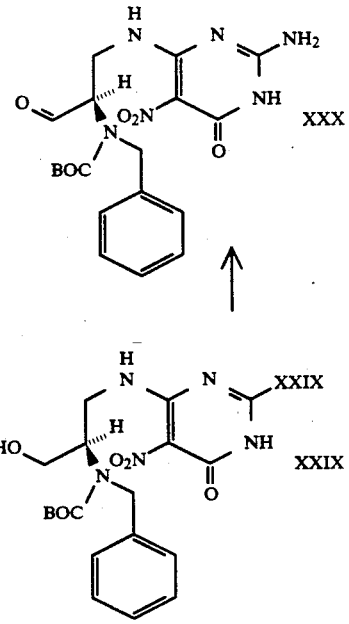

contain 25.6 mmol XXVII (56%). Another 6.3 mmol remained in the aqueous layer. A reverse phase chromatogram of the o-phthalaldehyde derivative of crude product showed greater than 99.5% of the fluorescence response in a single peak.

A sample of the oil was further purified by distillation at 95° C. and approximately 50 mm pressure, and precipitation of the dihydrochloride salt from MeOH/HCL with Et$_2$O: $^1$H NMR δ 3.2–3.7 (m, 3 H, —CH$_2$—NH$_2$, CH—NH), 3.86 (m, 2 H, O—CH$_2$), 4.29 (m, 2 H, benzyl), 7.4–7.8 (m, 5 H, Ar); $^{13}$C NMR δ ~39(submersed under DMSO), 47.7, 55.7, 56.5, 128.5, 128.8, 130.2, 131.7; MS (E.I., direct insertion) m/z (% relative abundance) 181(MH+)(1), 164(1), 150(87), 106(6), 91(100); HRMS (+DCI, CH$_4$) m/z calcd for C$_{10}$H$_{17}$N$_2$O(MH+) 181.134, found 181.135.

2-Amino-6-[((2'R)-Benzylamino-3'-Hydroxypropyl)amino]-5-nitro-4 (3H)-pyrimidinone (XXVIII). 2-Amino-6-chloro-5-nitro-4(3H)-pyrimidinone (14 g) was partially dissolved in 900 mL hot EtOH$_{abs}$ and filtered. To the filtrate, determined to contain 40 mmol of the pyrimidine, N,N-diisopropyl-ethylamine was added to achieve pH 8, and the mixture taken to reflux. A solution of 38 mmol XXVII (12.3 g crude material) in 100 mL EtOH was added all at once, and refluxed for 2 h with stirring while monitoring by cation exchange HPLC. Solvent was then distilled off until 700 mL remained, and then refrigerated overnight. A first crop collected by weighed after drying 9.56 g (containing 21.3 mmol product), with 12.8 mmol remaining in the filtrate (90% total). Further concentration of the filtrate produced two more crops with a combined weight of 4.44 g (containing 6.06 mmol XXVIII). All three crops were purified by suspension in ice-cold water. The collected precipitates were dried to give 12.86 g (containing 26.5 mmol) light yellow powder (70%).

Crude product was again suspended in water at 0° C., and filtered. The precipitate was partially dissolved in boiling EtOH (300 mL/g), filtered while still warm, and dried to give a light yellow powder: UV(λ$_{max}$) (0.1N HCL) 334 nm (ε=15,100), 286 nm (sh), 236 nm, (ε=13,400); (0.1M KPO$_4$pH 6.5) same as 0.1N HCL; (0.1N NaOH) 347 nm (ε=16,600), 232 nm (sh); $^1$H NMR δ 2.85 (m, 1 H, —NH—), 3.3–3.75 (m, 5 H, O—CH$_2$CHNCH$_2$N—), 3.85 (m, 2 H, benzyl), 7.1–7.5 (m, 7, Ar, NH$_2$), 9.83 (br, 1 H, CONH); $^{13}$C NMR δ 41.3, 49.8, 56.9, 60.7, 110.5, 126.8, 128.0, 128.2, 139.5, 154.0, 156.3, 159.0; MS (E.I., direct insertion) m/z(% relative abundance) 335(MH+)(0.5), 303(2), 167(8), 150(75), 91(100); HRMS (+DCI, CH$_4$) m/z calcd for C$_{14}$H$_{19}$N$_6$O$_4$(MH+) 335.147, found 335.146.

2-Amino-6-[[(2'R)-(N-t-BOC-benzylamino)-3'-hydroxypropyl]amino]-5-nitro-4(3H)-pyrimidinone (XXIX). A slurry of 10.3 mmol XXVIII (5 g combined crude material) in 200 mL dioxane was cooled on ice, and 1M NaOH added slowly to give pH 9.5 (26 mL). Di-t-butyl-dicarbonate 97% (2.5 g, 11.1 mmol) was added, the clear solution warmed to room temperature, and stirred well. At 3, 5.5, and 23 h the pH was readjusted with 1M NaOH and 0.3 g di-t-butyl-dicarbonate added. Cation exchange HPLC showed 4% XXVIII remaining at 46 h, and the reaction was then filtered and evaporated to remove the dioxane. The aqueous solution was adjusted to pH 7 with glacial acetic acid, and kept over night on ice. The precipitate was collected by centrifugation, resuspended in 10 mL ice-cold water, recentrifuged, and dried to give 5.64 g light yellow powder weighing (containing 9.6 mmol of XXIX, 93%), with an additional 0.3 mmol remaining in the aqueous supernates.

A sample of crude product was purified by preparative reverse phase HPLC: UV(λ$_{max}$) (0.1M HCL, 0.1M NH$_4$PO$_4$ pH 2.8, 0.1M KPO$_4$ pH 6.505) 335 nm (ε=13,300), ~288 nm (sh), 260 nm (min.), ~233 nm (sh); (0.1M NaOH) 346 nm (ε=15,600); $^1$H NMR δ 1.33 (br s, 9, C(CH$_3$)$_3$), 3.0–3.9 (5 H, CH—N, O—CH$_2$, N—CH$_2$), 4.39 (s, 2H, benzyl), 7.8–8.4 (br s, 7, Ar, NH$_2$), 10.4 (br, 1 H, CONH); MS (E.I., direct insertion) m/z (% relative abundance) 435(MH+)(0.25), 410(0.4), 404(2), 360(4), 303(1), 250(9), 194(15), 167(12), 150(75), 91(100); HRMS (+DCI, CH$_4$) m/z calcd for C$_{19}$H$_{27}$N$_6$O$_6$(MH+) 435.199, found 435.197.

N-[4-[(2S)-(N-t-BOC-benzylamino)-3-[(2-amino-5-nitro-4(3H)-oxo-pyrimidin-6-yl)amino]propylamino]-benzoyl]-L-glutamic acid (XXXI). To a solution of 5.0 g crude XXIX (8.51 mmol) in 125 mL dry $CH_2Cl_2$ was added 8.49 g 1,1,1-tris(acetoxy)-1,1-dihydro-1,2-benziodoxol-3(1H)-one (19.2 mmol+some HOAc) in 32 mL dry $CH_2Cl_2$ while stirring at room temperature under argon. The alcohol XXIX was completely consumed by 70 min as determined by reverse phase HPLC, and the reaction then poured into a mixture of 1M $NaHCO_3$ (76 mL) and 0.125M $Na_2S_2O_3$ (500 mL) and stirred for 15 min. The organic layer was washed with 250 mL $H_2O$, dried briefly ($Na_2SO_4$), solvent removed, and product dried to give 5.01 g yellow semisolid. A minimum yield of the aldehyde XXX was determined by reduction of a small sample with $NaBH_4$ in $DMF/H_2O$ (1:1) back to the alcohol XXIX which gave 93% of the expected amount. The chromatographic profile of the aldehyde XXX suggested an on-column equilibration with the hydrate. Stopped flow U.V. in pH 2.7 eluqnt showed $\lambda max=335$ nm, 288 nm (sh), 260 nm (min), 233 nm (sh). The product of this reaction, which was free of reagent by-products, was utilized immediately for reductive alkylation.

Crude aldehyde XXX (7.91 mmol) was dissolved in 28.5 mL DMF and cooled to 0° C. To this was rapidly added with stirring an ice-cold solution of 12 g (45 mmol) p-amino-benzoyl-L-glutamate (PABA-glu) dissolved in 40 mL DMF. After 5 min, a cold solution of 0.57 g $NaBH_3CN$ (95%, 8.6 mmol) in 8.2 mL DMF was quickly added, and the mixture stirred for 1 h. Analysis of the reaction by reverse phase HPLC showed 5.92 mmol of product (75%), no aldehyde XXX, and 0.45 mmol of alcohol XXIX. Solvent was removed, and ice-cold water (90 mL) added. The resulting slurry was adjusted to pH 2.5 with $HCl_{conc}$, centrifuged, and the precipitate dried. The supernate contained 0.45 mmol of product and the bulk of the excess PABA-glu. The resulting 6.27 g of yellow powder was mostly dissolved in 350 mL $EtOH_{abs}$ at 60° C. and filtered. The filtrate was concentrated under reduced pressure, rewarmed, and 2.5 volumes water added. After cooling, the precipitate was collected by centrifugation, and dried giving 4.56 g light yellow powder containing 4.35 mmol of XXXI (51% from XXIX).

A sample was purified by semi-preparative reverse phase HPLC: UV($\lambda_{max}$) (0.1M $NH_4PO_4$ pH 2.8) 301 nm ($\epsilon=23,900$), 335 (sh); (0.1M $KPO_4$, pH 6.5) 297 nm ($\epsilon=23,300$), 335 (sh); (0.1M NaOH) 299 nm ($\epsilon=23,200$), 347 nm ($\epsilon=16,000$); $^1$H NMR $\delta$ 1.29 (br s, 9, C(CH$_3$)$_3$), 2.00 (m, 2 H, $\beta$—CH$_2$), 2.33 (t, 2 H, $\gamma$—CH$_2$), 3.0–4.0 (5 H, CH—NH, Pyr—NH—CH$_2$, Ph—NH—CH$_2$), 4.0–4.7 (3 H, benzyl, $\alpha$—CH), 6.53 (d, 2 H, 3',5'-H), 7.22 (br s, 5 H, Ar), 7.66 (d, 2 H, 2',6'-H), 8.10 (d, 1 H, CONHCH), 9.45 (br s, 1 H, CONH); HRMS (FAB, Xe, glycerol/KTFA) m/z calcd for $C_{31}H_{36}N_8O_{10}K(MK^+)$ 719.219, found 719.233.

N-[4-[(2S)-benzylamino-3-[(2-amino-5-nitro-4(3H)-oxo-pyrimidin-6-yl)amino]propylamino]benzoyl]-L-glutamic acid (XXXII). A slurry of 3.87 g crude XXXI (3.69 mmol) in 39 mL THF plus 156 mL 1M HCL was heated to 58° C. with good stirring, resulting after 45 min in a clear solution. Analysis by reverse phase HPLC showed the $t_{\frac{1}{2}}$ of hydrolysis to be 19 min. At 150 min (with 99.4% conversion) the reaction was cooled, solvent removed, and the residue dried to give 3.51 g (containing 3.65 mmol XXXII). This material was extracted at 60° C. with water (110 mL), leaving a residue containing 0.57 mmol of product. The extract was taken to pH 3.1 with 10M NaOH and cooled for 18 h at 4° C. The resulting precipitate was collected and dried to give 2.17 g light yellow powder (containing 3.04 mmol XXXII) (3.61 mmol total, 98%). HPLC analysis of both the unextracted residue and the pH 3.1 precipitate showed more than 98% of the absorbance area at 295 nm within a single peak.

A sample was further purified by semi-preparative reverse phase HPLC: UV($\lambda_{max}$) (0.1M $NH_4PO_4$ pH 2.8) 292 nm, 332 nm; (0.1M $KPO_4$ pH 6.5) 290 nm, 332 nm; (0.1M NaOH) 300 nm ($\epsilon=22,300$), 346 nm ($\epsilon=16,500$); $^1$H NMR $\delta$ 2.02 (m, 2 H, $\beta$—CH$_2$), 2.34 (t, 2 H, $\gamma$—CH$_2$), 2.8–3.8 (5 H, CH—NH, Pyr—NH—CH$_2$, Ph—NH—CH$_2$), 3.90 (s, 2 H, benzyl), 4.32 (m, 1 H, $\alpha$—CH), 6.60 (d, 2 H, 3',5'-H), 7.15–7.5 (5 H, Ar), 7.67 (d, 2H, 2',6'-H), 8.14 (d, 1 H, CONHCH), 9.88 (br s, 1 H, CONH); HRMS (FAB, Xe, glycerol/PEG400) calcd for $C_{26}H_{31}N_8O_8(MH^+)$ 583.226, found 583.228.

N-[4-[((2S)-amino)-3-[(2,5-diamino-4(3H)-oxo-pyrimidin-6-yl)amino]propylamino]benzoyl]-L-glutamic acid (XVIb). To a clear solution of 1.05 g partially purified XXXII (1.47 mmol) in 45 mL DMF and 180 mL 0.1M HCl was added 1.05 g 10% Pd/C, and the mixture stirred vigorously under 45 psi $H_2$. Analysis at 25 h by cation exchange HPLC showed complete consumption of the starting material and less than 1% of the benzyl derivative of XVIb. With the reaction still under an atmosphere of hydrogen, the mixture was filtered as described for XVIa, and deaerated 0.01M HCl (10 mL) used to further wash product from the catalyst. The clear light yellow filtrate was quickly sparged with argon. HPLC analysis of this material showed that 99% of the electrochemical response in the chromatogram was located in a single peak, and titration with DCIP indicated 1.34 mmol of product. This 91% yield was confirmed by UV spectra in 0.1M HCl. Solvent was removed, and product redissolved in 30 mL deaerated 0.01M HCl.

A sample of crude product was purified on a semi-preparative reverse phase HPLC column pretreated with $Na_2S_2O_4$ to eliminate adsorbed oxygen: UV($\lambda max$) (0.1M HCl) 214 nm, 274 nm ($\epsilon=23,500$), 293 nm (sh); HRMS (FAB, Xe, glycerol/PEG400/DMF) calcd for $C_{19}H_{27}N_8O_6(MH^+)$ 463.205, found 463.208.

(6S)-Tetrahydrofolic acid (XXIIb). A solution of crude XVIb (1.34 mmol) in 30 mL 0.01M HCl was cooled to 18° C., and 33 mL of 50 mM $I_2$ in MeOH (1.65 mmol) was added over 10 s with good stirring, with a consequent increase in temperature to 27° C. After 2.0 min, the mixture was cooled within 2.7 min to −20° C. This temperature was maintained during subsequent titration to pH 9.2 (measured without dilution) with 10M NaOH over a period of 1.5 min. The reaction was rapidly warmed to 0° C., and at the same time sparged vigorously with argon. After 3.0 min at 0° C., 58 mL of 0.1M $Na_2S_2O_4$ (freshly dissolved in deaerated water) was added all at once with stirring, followed 2.0 min later by 0.82 mL 2-mercaptoethanol (11.7 mmol). Analysis by cation exchange HPLC indicated 0.74 mmol of tetrahydrofolic acid (55%). Contaminating impurities included small amounts of 7,8-dihydrofolic acid (XXIIIb), XIXb ($\lambda_{max}=290$ nm, pH 3.0), PABA-glu, and trace N5,N10-methylene-tetrahydrofolic acid, with 74% of the 285 nm absorbance area located in the peak of desired product.

The enantiomeric purity of this material was established by collecting the entire peak of tetrahydrofolic acid from an analytical HPLC separation, and reinjection onto a chiral HPLC column eluted with a buffer containing formaldehyde. Comparison of the resulting N5,N10-methylene derivative with the peaks produced by racemic (6R,S)-L-tetrahydrofolic acid ($R_s=1.5$) showed 97.0 to 97.5% enantiomeric purity.

Crude (6S)-tetrahydrofolate can be purified (with 90% recovery) from salts and most by-products by chromatography on anion exchange cellulose using dilute 2-mercaptoethanol with increasing concentrations of HCl as eluant. Eluant is removed, after addition of DMF, by evaporation to a volume less than that of the added DMF, and product precipitated with $Et_2O$. The chromatographic properties, UV and mass spectra of this material were found to be identical to authentic tetrahydrofolic acid.

Example 2a: Synthesis of the Unnatural (6R)-Enantiomer of Tetrahydrofolic Acid The above series of experiments were repeated starting with D-serine methyl ester with similar results yielding (6R)-tetrahydrofolic acid (97 to 98% enantiomeric purity).

Example 3: Synthesis of N5-Formyl-tetrahydrofolic Acid (Leucovorin)

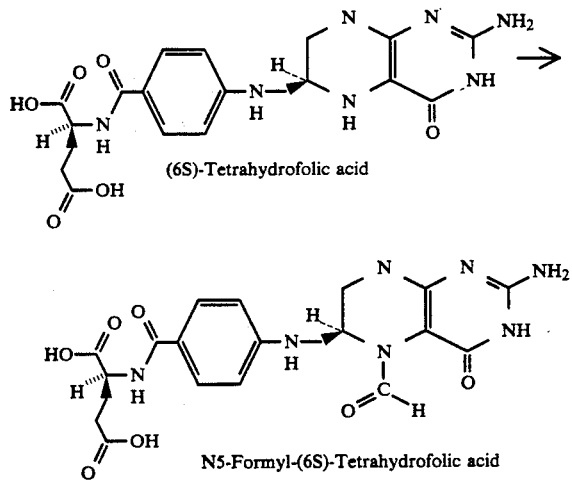

N5-Formyl-tetrahydrofolic acid (Leucovorin). Tetrahydrofolic acid trihydrochloride, 0.50 g (0.90 mmol) was dissolved in 45 mL of dry DMF, 0.17 mL 98% formic acid (4.5 mmol) added, and the clear solution sparged with argon. To this was added 0.39 g (2.40 mmol) 1,1′-carbonyl diimidazole (CDI) in three portions with vigorous stirring under inert atmosphere. Ion pair HPLC analysis showed 0.82 mmol of N5-formyl-tetrahydrofolate with 3% tetrahydrofolate remaining. No 7,8-dihydrofolate or N5,N10-methylene-tetrahydrofolate was detected, and N5,N10-methenyl-and N10-formyl-tetrahydrofolate were both less than 1% of the total absorbance of the chromatogram. The reaction mixture was diluted with $Et_2O$, and the resulting precipitate collected by centrifugation. After decanting the supernate and brief exposure to vacuum, to the resulting gum was added 0.12 g $CaCl_2.2H_2O$ (0.82 mmol) in 12 mL water. The suspension, which was mostly dissolved by neutralization to pH 7 with 10M NaOH, was centrifuged to remove a brown precipitate, and 25 mL EtOH added. After refrigeration, product was collected by centrifugation, washed with cold EtOH, and dried to 0.452 g containing 0.61 mmol leucovorin (68%). A chromatogram of this material showed that greater than 99% of the 285 nm absorbance resided in a single peak.

N5-Formyl-(6S)-tetrahydrofolic acid (Natural Leucovorin). A crude reaction mixture containing 0.056 mmol of (6S)-tetrahydrofolic acid (XXIIb) was evaporated together with 40 mL DMF to a final volume of 10.4 mL. The resulting slurry was mostly solubilized by addition of 1% v/v of 98% formic acid. After centrifugation, the supernate was found to contain 0.042 mmol of XXIIb, the remainder being associated with the undissolved salts. The clear supernate was sparged with argon, and 13.6 mg (0.084 mmol) CDI dissolved in dry DMF added in two aliquots with vigorous stirring. Analysis by HPLC showed 0.035 mmol of N5-formyl-(6S)-tetrahydrofolic acid, with 8% of starting material remaining. The chromatographic properties, UV and mass spectra were identical to authentic material.

The enantiomeric purity of this material was established by chiral HPLC which showed 97.0 to 97.5% enantiomeric purity, the same as the starting (6S)-tetrahydrofolic acid. Thus, no racemization occurs due to this formylation.

Conclusion, Ramifications and Scope of Invention

Thus the reader will see that the process and the intermediates of this invention provide for the C6-stereospecific chemical synthesis of valuable tetrahydropteridines, such as the biologically active forms of the vitamin folic acid, (6S)-tetrahydrofolic acid and its N5-formyl derivative. The invention provides for the convenient preparation of 6-monosubstituted tetrahydropteridines with high enantiomeric purity in good yield from inexpensive starting material. It allows the synthesis of either the natural or unnatural isomer from a wide range of available precursors. It is implementable on a large scale, and thus can generate the natural isomers of several drugs currently being used primarily as racemic mixtures.

A further aspect of this invention provides a rapid, one-step, high yield method for formylation of tetrahydropteridines. This method is highly regiospecific for formylation of N5, for example in the preparation of N5-formyl-(6S)-tetrahydrofolic acid. The reagents are inexpensive and give a product of high chemical purity without producing detectable racemization.

Although the description above contains many specificities, these should not be construed as limiting the scope of the invention, but as merely providing illustrations of some of the presently preferred embodiments of this invention. Many other variations are possible. For example, $R_3$ may contain additional chiral centers in addition to that which becomes C6 in the tetrahydropteridine. These are obtained either in the preparation of the diamines (III) or (III′) or by modification of $R_3$ subsequent to condensation with pyrimidine. Further, the invention is not limited to the production of the 5-keto-pyrimidine (II) or (II′) from the 5-imino-pyrimidine (I) or (I′), respectively, although this is a preferred method. Further, the 6-substituent can be elaborated after cyclization and reduction of an intermediate (I), (I′), (II), or (II′) to a 6-monosubstituted tetrahydropteridine C6-stereoisomer. For example, where $R_3$ is initially a protected aldehyde, following formation of the initial tetrahydropteridine, the aldehyde is deprotected for subsequent condensation with, for example, a p-aminobenzoyl derivative. Further, the tetrahydropteridines prepared from intermediates (I), (I'), (II), or (II') can be derivatized by known procedures to produce other useful compounds, for example, N5-methyl and N5,N10-methylene tetrahydrofolic acid derivatives.

We claim:

1. A process for the selective formylation of nitrogen-5 in a tetrahydropteridine which contains a p-aminobenzoyl moiety as a constituent of said tetrahydropteridine's 6-substituent comprising treating a solution of said tetrahydropteridine in a largely aprotic solvent with an imidazole-based formylating reagent.

2. The method of claim 1 wherein said imidazole-based formylating reagent is N-formyl-imidazole.

3. The method of claim 1 wherein said imidazole-based formylating reagent is formic acid and 1,1'-carbonyl-diimidazole.

4. The method of claim 1 wherein said treating comprises adding 1,1'-carbonyl-diimidazole to a solution of (6S)-tetrahydrofolic acid and formic acid in substantially dry N,N-dimethyl-formamide, whereby N5-Formyl-(6S)-tetrahydrofolic acid is produced.

* * * * *